(12) United States Patent
Golovko et al.

(10) Patent No.: US 11,352,884 B2
(45) Date of Patent: Jun. 7, 2022

(54) DOWNHOLE HYDROGEN SULFIDE CAPTURE AND MEASUREMENT

(71) Applicant: Halliburton Energy Services, Inc., Houston, TX (US)

(72) Inventors: Julia Golovko, Houston, TX (US); James M. Price, Cypress, TX (US); Christopher Michael Jones, Katy, TX (US); Anthony Herman Van Zuilekom, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 72 days.

(21) Appl. No.: 16/442,626

(22) Filed: Jun. 17, 2019

(65) Prior Publication Data
US 2020/0392843 A1 Dec. 17, 2020

(51) Int. Cl.
| | |
|---|---|
| *E21B 49/10* | (2006.01) |
| *G01N 1/22* | (2006.01) |
| *G01N 33/00* | (2006.01) |
| *E21B 49/08* | (2006.01) |
| *E21B 47/06* | (2012.01) |
| *E21B 47/07* | (2012.01) |

(52) U.S. Cl.
CPC .......... *E21B 49/10* (2013.01); *E21B 49/081* (2013.01); *G01N 1/2214* (2013.01); *G01N 1/2226* (2013.01); *G01N 33/0044* (2013.01); *E21B 47/06* (2013.01); *E21B 47/07* (2020.05); *E21B 49/0875* (2020.05)

(58) Field of Classification Search
CPC ..... E21B 49/10; E21B 49/081; G01N 1/2214; G01N 33/0044
See application file for complete search history.

(56) References Cited

U.S. PATENT DOCUMENTS

| | | | | |
|---|---|---|---|---|
| 6,416,994 | B1 * | 7/2002 | Uruga ................. | C02F 3/28 |
| | | | | 435/287.5 |
| 7,219,541 | B2 * | 5/2007 | DiFoggio .......... | G01N 33/2823 |
| | | | | 73/152.25 |
| 10,882,741 | B2 * | 1/2021 | Monteiro ............. | B82Y 30/00 |
| 2001/0016184 | A1 * | 8/2001 | Campbell ............. | B01J 23/56 |
| | | | | 502/355 |
| 2002/0121370 | A1 * | 9/2002 | Kurkjian .............. | E21B 49/081 |
| | | | | 166/250.01 |

(Continued)

FOREIGN PATENT DOCUMENTS

| | | | | |
|---|---|---|---|---|
| WO | 2017106708 | | 6/2017 | |
| WO | WO-2018063141 | A1 * | 4/2018 | ............. E21B 49/10 |
| WO | 2018118017 | | 6/2018 | |

OTHER PUBLICATIONS

International Search Report and Written Opinion for Application No. PCT/US2019/037459, dated Mar. 16, 2020.

(Continued)

*Primary Examiner* — Blake Michener
(74) *Attorney, Agent, or Firm* — John Wustenberg; C. Tumey Law Group PLLC (57) ABSTRACT

Disclosed herein are methods and systems for capture and measurement of a target component. A fluid sampling tool for sampling fluid from a subterranean formation may include a sample chamber having a fluid inlet, wherein the sample chamber is lined with a coating of a material that can reversibly hold a target component.

20 Claims, 6 Drawing Sheets

(56) References Cited

U.S. PATENT DOCUMENTS

| | | | |
|---|---|---|---|
| 2003/0033866 A1* | 2/2003 | Diakonov | E21B 49/081 73/152.55 |
| 2004/0089079 A1* | 5/2004 | Engebretson | E21B 49/084 73/863.23 |
| 2005/0112027 A1 | 5/2005 | Arii et al. | |
| 2006/0032301 A1* | 2/2006 | DiFoggio | G01N 29/036 73/152.18 |
| 2006/0054501 A1* | 3/2006 | Jiang | G01N 33/0044 436/28 |
| 2010/0252258 A1 | 10/2010 | Pelletier | |
| 2012/0223226 A1* | 9/2012 | Rafferty | G01N 1/405 250/288 |
| 2014/0338900 A1* | 11/2014 | Jones | E21B 49/00 166/264 |
| 2016/0215617 A1 | 7/2016 | Samec et al. | |
| 2017/0260827 A1 | 9/2017 | Hopkins et al. | |
| 2017/0261408 A1* | 9/2017 | Cardin | G01N 30/14 |
| 2017/0285211 A1 | 10/2017 | Monteiro et al. | |
| 2018/0328172 A1* | 11/2018 | Pelletier | E21B 49/086 |
| 2018/0340418 A1 | 11/2018 | Perkins et al. | |
| 2019/0078418 A1 | 3/2019 | Jones et al. | |
| 2019/0284934 A1* | 9/2019 | Perkins | E21B 49/0875 |
| 2020/0408092 A1* | 12/2020 | Jones | E21B 49/00 |

OTHER PUBLICATIONS

Halliburton Reservoir Description Tool (RDT™) Formation Tester, Halliburton, 2016.
GeoTap® Formation Pressure Tester Service, Halliburton, 2017.
GeoTap® IDS Sensor, Halliburton, 2016.

\* cited by examiner

DOWNHOLE HYDROGEN SULFIDE CAPTURE AND MEASUREMENT

BACKGROUND

Wells may be drilled at various depths to access and produce oil, gas, minerals, and other naturally-occurring deposits from subterranean geological formations. The drilling of a well is typically accomplished with a drill bit that is rotated within the well to advance the well by removing topsoil, sand, clay, limestone, calcites, dolomites, or other materials. The drill bit is typically attached to a drill string that may be rotated to drive the drill bit and within which drilling fluid, referred to as "drilling mud" or "mud", may be delivered downhole. The drilling mud is used to cool and lubricate the drill bit and downhole equipment and is also used to transport any rock fragments or other cuttings to the surface of the well.

It is often desired to collect a representative sample of formation or reservoir fluids (e.g., hydrocarbons) to further evaluate drilling operations and production potential, or to detect the presence of certain gases or other materials in the formation that may affect well performance. For example, hydrogen sulfide ($H_2S$), a poisonous, corrosive, and flammable gas can occur in formation fluids, and its presence in the wellbore in significant concentrations may result in damage to wellbore components or dangerous conditions for well operators at the surface. However, $H_2S$ concentration in formation fluids is often underestimated with current measurement techniques, for example, due to losses via absorption/adsorption on tool surfaces and/or during sample transfers.

BRIEF DESCRIPTION OF THE DRAWINGS

The features and advantages of certain embodiments will be more readily appreciated when considered in conjunction with the accompanying figures. The figures are not to be construed as limiting any of the preferred embodiments.

DETAILED DESCRIPTION

The present disclosure relates to subterranean operations and, more particularly, embodiments disclosed herein provide methods and systems for capture and measurement of a target component.

Embodiments may include sampling of formation fluids from a wellbore to determine a concentration of a target component in the formation fluid. Target component may include any of a variety of gases, vapors, or liquids, where quantification in formations fluids may be desired, including, but not limited to, $H_2S$, mercury, and carbon dioxide, among others. By way of example, $H_2S$ is a volatile chemical that oxidizes easily, is corrosive to downhole tools, and is poisonous and explosive. The presence of $H_2S$ in a formation may increase the cost of extracting and processing formation fluids from a well and also present a safety hazard to well operators. Accurate measurement of $H_2S$ (or other target components) in the formation fluids can better enable well operators to make decisions about completing a well so that formation fluids can be economically extracted while maintaining safe conditions for well operators. In addition, it may desirable to know concentration of mercury and carbon dioxide as well, as these components can also be corrosive.

The fluid sampling tools described herein may vary in design, but embodiments of the fluid sampling tools typically may include an inlet, an outlet, and a sampling chamber. Embodiments may further include two or more sampling chambers. The inlet and outlet may be fluidly connected to the fluid within the wellbore that is being extracted from a subterranean formation. In operation, a fluid sample may be gathered into the sampling chamber from the wellbore for analysis. Embodiments may include coating inner surfaces of the sampling chamber with a material that can reversibly sorb the target component. In this manner, the target component in the fluid sample should be sorbed by the coating, instead of being lost via sorbtion on tool surfaces. At a desired time, for example, after recovery of the sample tool to the well surface, the target component can be desorbed and measured. Given a known volume of formation fluid sampled and amount of target component, the concentration of the target component in the sample can be determined. Multiple component measurements from multiple sample chambers (e.g., two or more) may be obtained, for example, to extrapolate to reservoir conditions. The component measurements may be obtained at different times in the wellbore.

The fluid sampling tools, systems and methods described herein may be used with any of the various techniques employed for evaluating a well, including without limitation wireline formation testing (WFT), measurement while drilling (MWD), and logging while drilling (LWD). The various tools and sampling units described herein may be delivered downhole as part of a wireline-delivered downhole assembly or as a part of a drill string. It should also be apparent that given the benefit of this disclosure, the apparatuses and methods described herein have applications in downhole operations other than drilling, and may also be used after a well is completed.

Figure 1A:
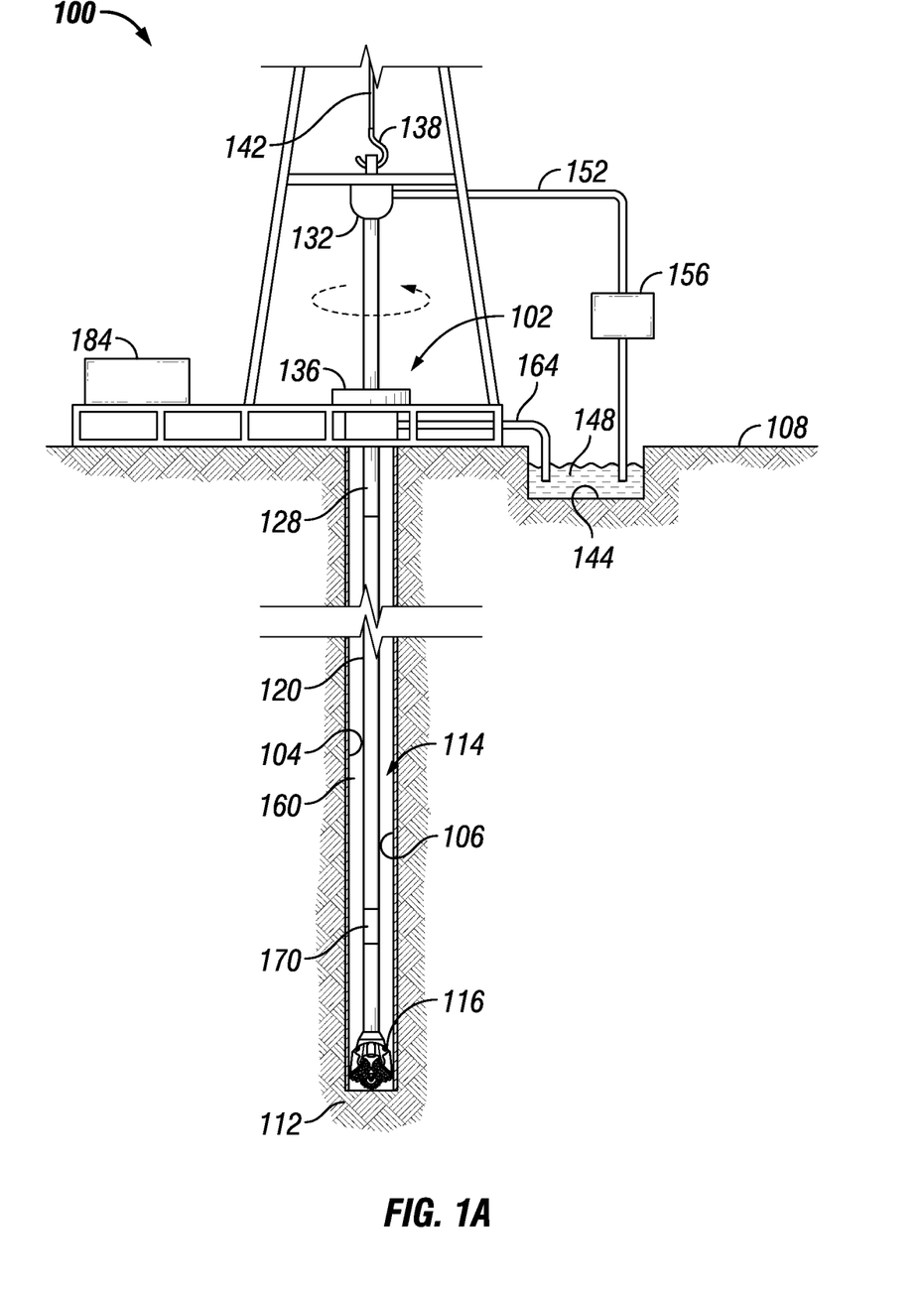
FIG. 1A illustrates a schematic view of a well in which an example embodiment of a fluid sample system is deployed.

FIG. 1A illustrates a fluid sampling and analysis system 100 according to an illustrative embodiment used in a well 102 having a wellbore 104 that extends from a surface 108 of the well 102 to or through a subterranean formation 112. While the wellbore 104 is shown extending generally vertically into the subterranean formation 112, the principles described herein are also applicable to wellbores that extend at an angle through the subterranean formations 112, such as horizontal and slanted wellbores. For example, although FIG. 1A shows wellbore 104 that is vertical or low inclination, high inclination angle or horizontal placement of the wellbore 104 and equipment is also possible. In addition, it should be noted that while FIG. 1A generally depicts a land-based operation, those skilled in the art should readily recognize that the principles described herein are equally applicable to subsea operations that employ floating or sea-based platforms and rigs, without departing from the scope of the disclosure.

The well 102 is illustrated with the fluid sampling and analysis system 100 being deployed in a drilling assembly 114. In the embodiment illustrated in FIG. 1A, the well 102 is formed by a drilling process in which a drill bit 116 is turned by a drill string 120 that extends from the drill bit 116 to the surface 108 of the well 102. The drill string 120 may be made up of one or more connected tubes or pipes, of varying or similar cross-section. The drill string 120 may refer to the collection of pipes or tubes as a single component, or alternatively to the individual pipes or tubes that include the string. The term "drill string" is not meant to be limiting in nature and may refer to any component or components that are capable of transferring rotational energy from the surface of the well to the drill bit. In several embodiments, the drill string 120 may include a central passage disposed longitudinally in the drill string 120 and capable of allowing fluid communication between the surface 108 of the well 102 and downhole locations.

At or near the surface 108 of the well 102, the drill string 120 may include or be coupled to a kelly 128. The kelly 128 may have a square, hexagonal, octagonal, or other suitable cross-section. The kelly 128 may be connected at one end to the remainder of the drill string 120 and at an opposite end to a rotary swivel 132. As illustrated, the kelly 120 may pass through a rotary table 136 that is capable of rotating the kelly 128 and thus the remainder of the drill string 120 and drill bit 116. The rotary swivel 132 should allow the kelly 128 to rotate without rotational motion being imparted to the rotary swivel 132. A hook 138, cable 142, traveling block (not shown), and hoist (not shown) may be provided to lift or lower the drill bit 116, drill string 120, kelly 128 and rotary swivel 132. The kelly 128 and swivel 132 may be raised or lowered as needed to add additional sections of tubing to the drill string 120 as the drill bit 116 advances, or to remove sections of tubing from the drill string 120 if removal of the drill string 120 and drill bit 116 from the well 102 is desired.

A reservoir 144 may be positioned at the surface 108 and holds drilling fluid 148 for delivery to the well 102 during drilling operations. A supply line 152 may fluidly couple the reservoir 144 and the inner passage of the drill string 120. A pump 156 may drive the drilling fluid 148 through the supply line 152 and downhole to lubricate the drill bit 116 during drilling and to carry cuttings from the drilling process back to the surface 108. After traveling downhole, the drilling fluid 148 returns to the surface 108 by way of an annulus 160 formed between the drill string 120 and the wellbore 104. At the surface 108, the drilling mud 148 may returned to the reservoir 144 through a return line 164. The drilling mud 148 may be filtered or otherwise processed prior to recirculation through the well 102.

Figure 1B:
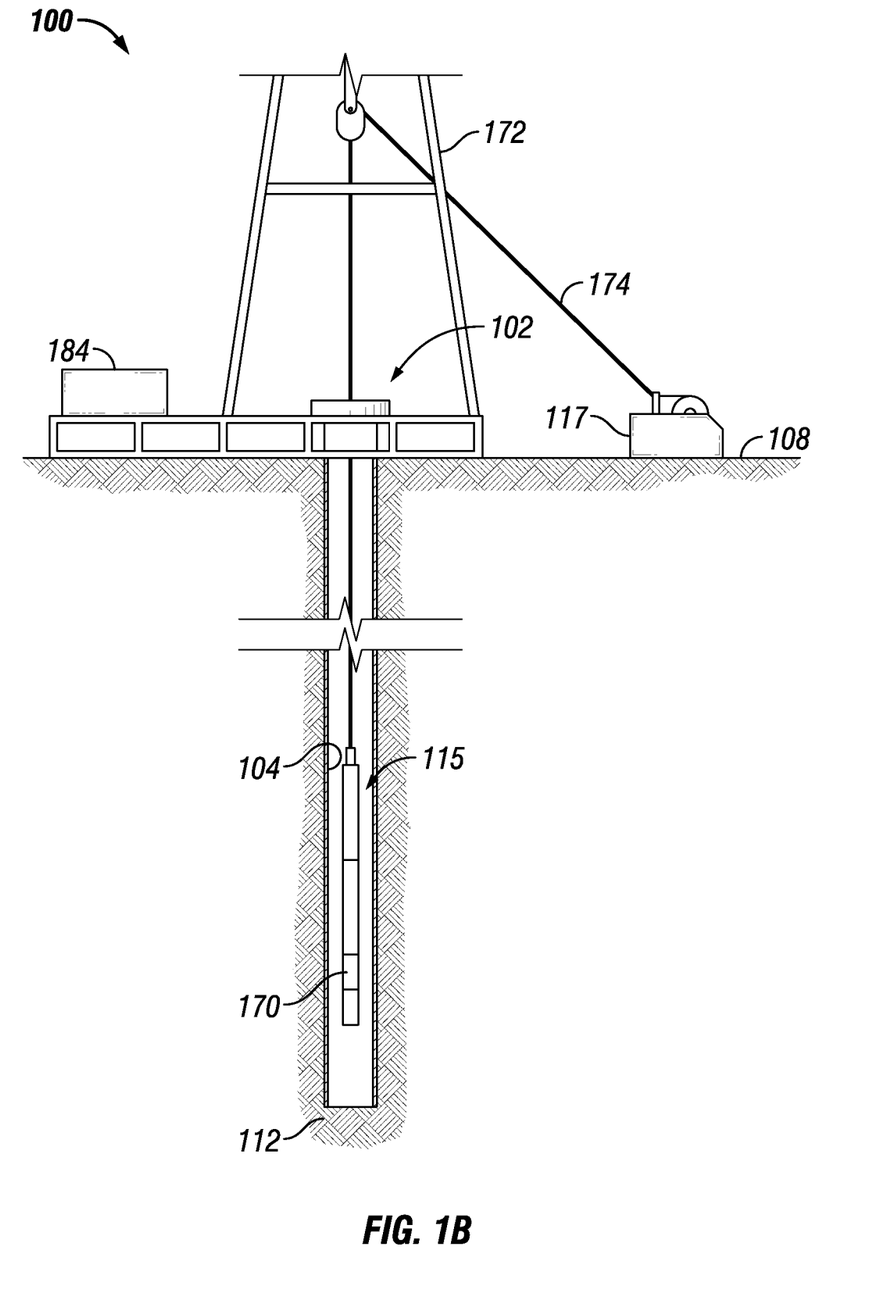
FIG. 1B illustrates a schematic view of another well in which an example embodiment of a fluid sample system is deployed.

FIG. 1B illustrates a schematic view of another embodiment of well 102 in which an example embodiment of fluid analysis system 100 may be deployed. As illustrated, fluid analysis system 100 may be deployed as part of a wireline assembly 115, either onshore of offshore. As illustrated, the wireline assembly 115 may include a winch 117 for example, to raise and lower a downhole portion of the wireline assembly 115 into the well 102. As illustrated, fluid analysis system 100 may include fluid sampling tool 170 attached to the winch 117. In examples, it should be noted that fluid sampling tool 170 may not be attached to a winch unit 104. Fluid sampling tool 170 may be supported by rig 172 at surface 108.

Fluid sampling tool 170 may be tethered to the winch 117 through wireline 174. While FIG. 1B illustrates wireline 174, it should be understood that other suitable conveyances may also be used for providing mechanical conveyance to fluid sampling tool in the well 102, including, but not limited to, slickline, coiled tubing, pipe, drill pipe, drill string, downhole tractor, or the like. In some examples, the conveyance may provide mechanical suspension, as well as electrical connectivity, for fluid sampling tool 170. Wireline 174 may include, in some instances, a plurality of electrical conductors extending from winch 117. By way of example, wireline 174 may include an inner core of seven electrical conductors (not shown) covered by an insulating wrap. An inner and outer steel armor sheath may be wrapped in a helix in opposite directions around the conductors. The electrical conductors may be used for communicating power and telemetry downhole to fluid sampling tool 170.

With reference to both FIGS. 1A and 1B, operation of fluid sampling tool 170 for sample collection will now be described in accordance with example embodiments. Fluid sampling tool 170 may be raised and lowered into well 102 on drill string 120 (FIG. 1A) and wireline 174. (FIG. 1B). Fluid sampling tool 170 may be positioned downhole to obtain fluid samples from the subterranean formation 112 for analysis. The formation fluid and, thus the fluid sample may be contaminated with, or otherwise contain, the target component. In some embodiments, the target component may be contained in the fluid sample in small quantities, for example, less than 500 parts per million ("ppm"). For example, the target component may be present in the fluid sample in an amount from about 1 ppm to about 500 ppm, about 100 ppm to about 200 ppm, about 1 ppm to about 100 ppm, or about 5 to about 10 ppm. The fluid sampling tool 170 may be operable to measure, process, and communicate data regarding the subterranean formation 112, fluid from the subterranean formation 112, or other operations occurring downhole. After recovery, the fluid sample may be analyzed, for example, to quantify the concentration of the target component. This information including information gathered from analysis of the fluid sample, allows well operators to determine, among other things, the concentration the target component within the fluid being extracted from the subterranean formation 112 to make intelligent decisions about ongoing operation of the well 102. In some embodiments, the data measured and collected by the fluid sampling tool 170 may include, without limitation, pressure, temperature, flow, acceleration (seismic and acoustic), and strain data. As described in more detail below, the fluid sampling tool 170 may include a communications subsystem, including a transceiver for communicating using mud pulse telemetry or another suitable method of wired or wireless communication with a surface controller 184. The transceiver may transmit data gathered by the fluid sampling tool 170 or receive instructions from a well operator via the surface controller 184 to operate the fluid sampling tool 170.

Figure 2:
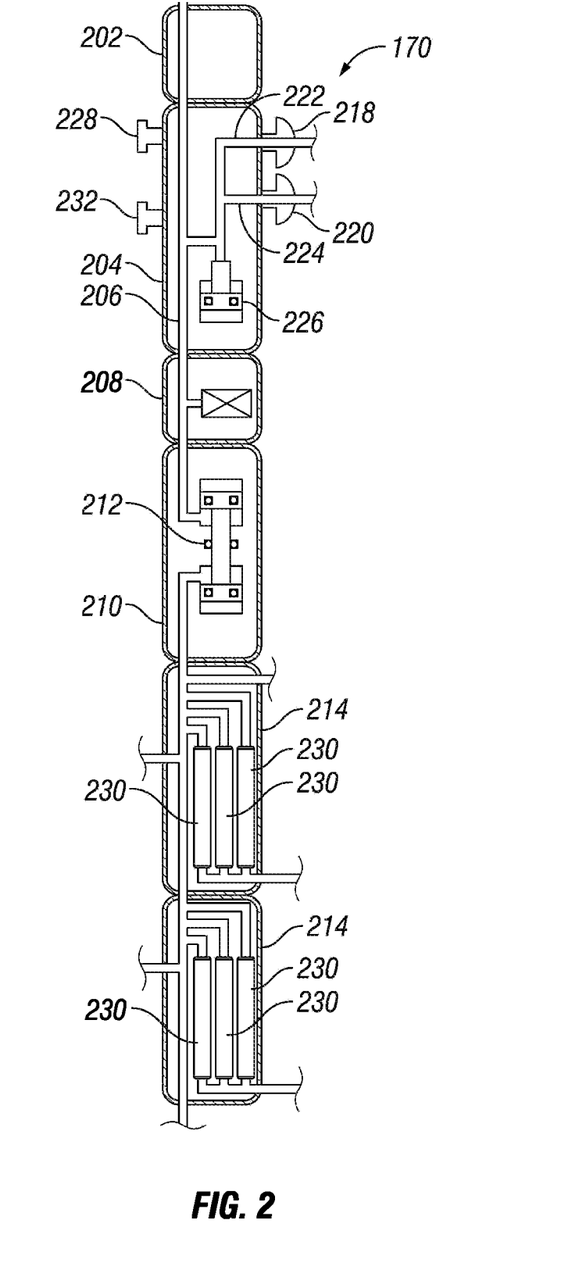
FIG. 2 illustrates a schematic view of an example embodiment of a fluid sampling tool.

Referring now to FIG. 2, an example embodiment of a fluid sampling tool 170 is illustrated as a tool for gathering fluid samples from a formation for subsequent analysis and testing. It should be understood that the fluid sampling tool 170 shown on FIG. 2 is merely illustrative and the example embodiments disclosed herein may be used with other tool configurations. In an embodiment, the fluid sampling tool 170 includes a transceiver 202 through which the fluid sampling tool 170 may communicate with other actuators and sensors in a conveyance (e.g., drill string 120 on FIG. 1A or wireline 174 on FIG. 1B), the conveyance's communications system, and with a surface controller (surface controller 184 on FIG. 1A). In an embodiment, the transceiver 202 is also the port through which various actuators (e.g. valves) and sensors (e.g., temperature and pressure sensors) in the fluid sampling tool 170 are controlled and monitored by, for example, a computer in another part of the conveyance or by the surface controller 184. In an embodiment, the transceiver 202 includes a computer that exercises the control and monitoring function.

The fluid sampling tool 170 may include a dual probe section 204, which extracts fluid from the formation (e.g., formation 112 on FIGS. 1A and 1B), as described in more detail below, and delivers it to a channel 206 that extends from one end of the fluid sampling tool 170 to the other. The channel 206 can be connected to other tools or portions of the fluid sampling tool 170 arranged in series. The fluid sampling tool 170 may also include a gauge section 208, which includes sensors to allow measurement of properties, such as temperature and pressure, of the fluid in the channel 206. The fluid sampling tool 170 may also include a flow-control pump-out section 210, which includes a pump 212 for pumping fluid through the channel 206. The fluid sampling tool 170 also includes one or more chambers, such as multi-chamber sections 214, which are described in more detail below.

In some embodiments, the dual probe section 204 includes two probes 218, 220 which extend from the fluid sampling tool 170 and press against the borehole wall to receive fluid for sampling. Probe channels 222, 224 connect the probes 218, 220 to the channel 206. The pump 212 can be used to pump fluids from the reservoir, through the probe channels 222, 224 and to the channel 206. Alternatively, a low volume pump 226 can be used for this purpose. Two standoffs or stabilizers 228, 232 hold the fluid sampling tool 170 in place as the probes 218, 220 press against the borehole wall to receive fluid. In an embodiment, the probes 218, 220 and stabilizers 228, 232 are retracted when the tool is in motion and are extended to gather samples of fluid from the formation.

Figure 3:
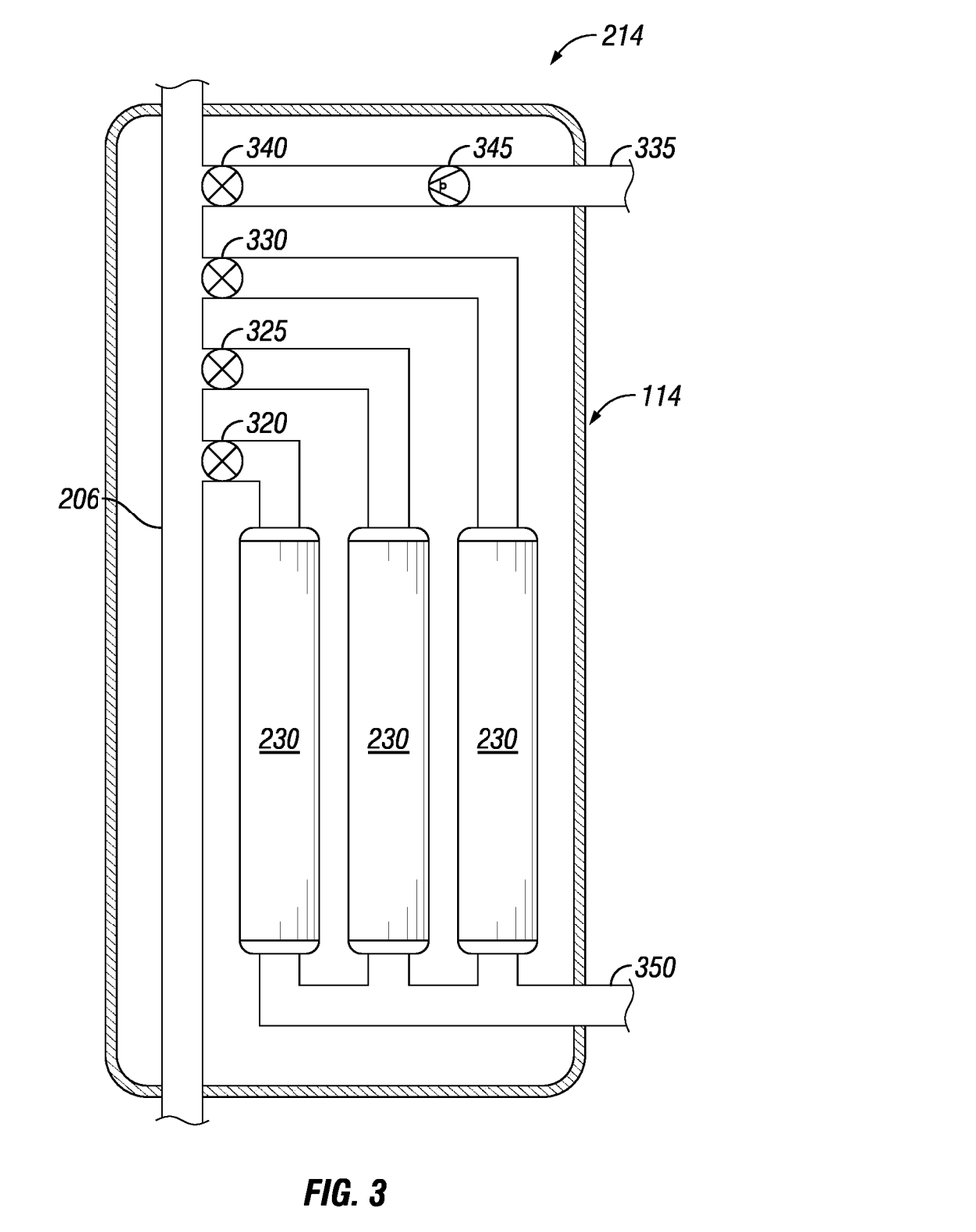
FIG. 3 illustrates an enlarged schematic view of an example embodiment the fluid sampling tool of FIG. 2

With additional reference to FIG. 3, the multi-chamber sections 214 include multiple sample chambers 230. While FIGS. 2 and 3 show the multi-chamber sections 214 having three sample chambers 230, it will be understood that the multi-chamber sections 214 can have any number of sample chambers 230 and may in fact be single chamber sections. In some embodiments, the sample chambers 230 may be coupled to the channel 206 through respective chamber valves 320, 325, 330. Formation fluid can be directed from the channel 206 to a selected one of the sample chambers 230 by opening the appropriate one of the chamber valves 320, 325, 330. The valves 320, 325, 330 may be configured such that when one of the chamber valves 320, 325, 330 is open the others are closed.

In some embodiments, the multi-chamber sections 214 may include a path 335 from the channel 206 to the annulus 160 through a valve 340. Valve 340 may be open during the draw-down period when the fluid sampling tool 170 is clearing mud cake, drilling mud, and other contaminants into the annulus before clean formation fluid is directed to one of the sample chambers 230. A check valve 345 prevent fluids from the annulus 160 from flowing back into the channel 206 through the path 335. As such, the multi-chamber sections 214 may include a path 350 from the sample chambers 230 to the annulus 160.

Figure 4:
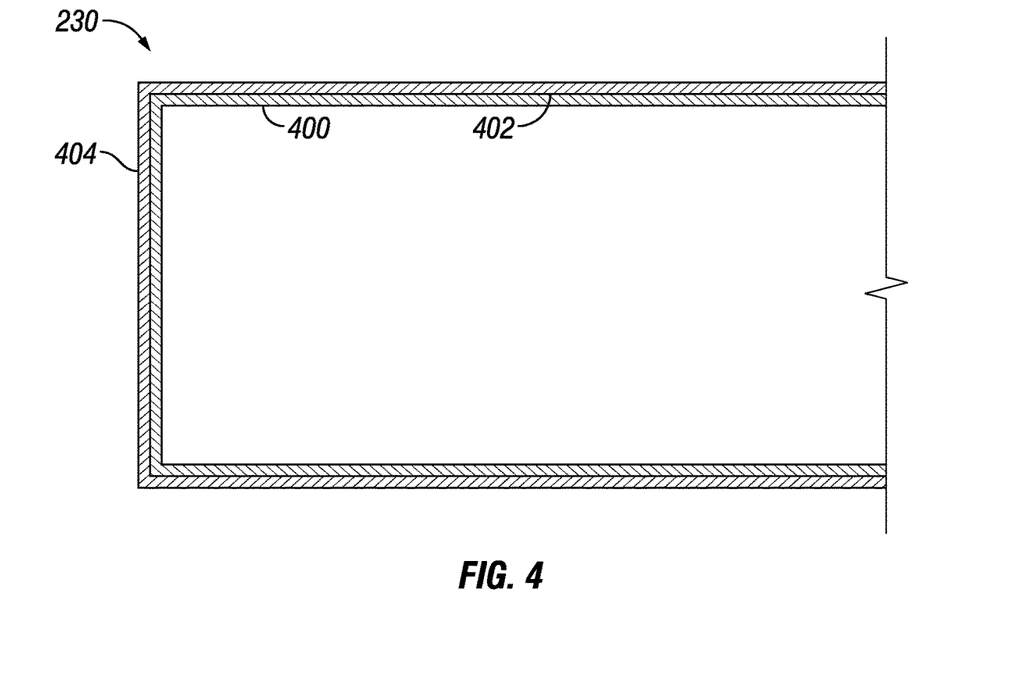
FIG. 4 illustrates a cross-sectional view an example embodiment of a sample chamber coated with a material that is reversibly sorbent.

FIG. 4 illustrates a cross-sectional view an example embodiment of a sample chamber 230 lined with a coating 400 of a material that can reversibly sorb a target component. As illustrated, the coating 400 may be disposed on inner surfaces 402 of chamber walls 404. Sample chamber 230 may be any suitable chamber for use in a fluid sampling tool (e.g., fluid sampling tool 170 on FIGS. 1A, 1B, and 2). In some embodiments, sample chamber 230 may have a fixed volume. For example, the sample chamber 230 may have a fixed volume of from about 0.1 milliliters to about 1 liter. Alternatively, the sample chamber 230 may have a fixed volume of from about 1 milliliters to about 1 liter. In some embodiments, the sample chamber 230 may be configured for obtaining micro-samples, i.e., volumes of less than 1 milliliter. For example, the sample chamber 230 may have a fixed volume of from about 10 milliliters to about 1 milliliters. One of ordinary skill in the art, with the benefit of this disclosure, should be able to select an appropriate sample chamber 230 and size thereof for a particular application.

As illustrated, the coating 400 may line the sample chamber 230. The coating 400 may include any of a variety of suitable materials capable of reversibly sorbing a target component, such as H2S, mercury, or carbon dioxide, whether by absorption or adsorption. Non-limiting examples of suitable materials may include, but are not limited to, gold, silver, nickel, platinum, and combinations thereof. In some embodiments, gold may be suitable for reversible absorption of target component, such as H2S and mercury. In some embodiments, nickel and/or platinum may be suitable for reversible absorption of H2S and/or mercury. One of ordinary skill in the art, with the benefit of this disclosure, should be able to select an appropriate material for the coating 400 based on a number of factors, including the particular target component of interest.

The coating 400 on the chamber walls 404 may have any suitable thickness. For example, the coating 400 may have a thickness of about 10 nm to about 100 microns. In some embodiments, the coating 400 may have a thickness of about 0.1 micron to about 1 micron or about 10 microns to about 100 microns. One of ordinary skill in the art, with the benefit of this disclosure, should be able to select an appropriate thickness for the coating 400 based on a number of factors, including the particular target component of interest and surface area.

The coating 400 may be applied to the chambers walls 404 using any suitable technique. Suitable techniques may include any of a variety of different techniques for depositing a coating onto a substrate, including, but not limited to thin-film deposition techniques, such as atomic layer deposition, physical vapor deposition, and chemical vapor deposition. One or ordinary skill in the art, with the benefit of this disclosure, should be able to select an appropriate technique for application of the coating 400.

It should be understood that the surface area of the coating 400 available for the target component may provide an upper limit on the amount of the target component that can be quantified. In other words, the fluid sample may, in some embodiments, contain more of the target component than can be sorbed by the coating 400. Accordingly, the surface of the coating 400 may be selected so that a sufficient quantity of target component can be measured to provide desirable information.

In some embodiments, the surface-to-volume ratio of the coating 400 and or the chamber walls 404 may be maximized, for example, to provide additional surface area for sorption of the target component. In this manner, the coating 400 and/or the chamber walls 404 may be configured to effective sorption of different concentrations of the target component. In some embodiments, the surface-to-volume ratio of the coating 400 may be maximized. In some embodiments, the surface-to-volume ratio of the chamber walls 404 may be maximized. In some embodiments, the surface-to-volume ratio of the coating 400 and the chamber walls 404 may be maximized. Any of a variety of techniques may be applied to the coating 400 and/or chamber walls 404 for maximization of the surface-to-volume ratio. Suitable examples of the coating 400 and/or chamber walls 404 with increased surface-to-volume ratio may include creation of a porous or structure coating that maximizes surface-to-volume ratio. Examples of suitable techniques for maximization of the surface-to-volume ratio may include, but are not limited to, lithograph techniques, such as etching, anodizing, or patterning. Specific examples of suitable lithograph techniques may include, but are not limited to, electro-chemical anodization, semiconductor lithography, and electron-beam lithography. In addition to lithographic techniques applied to the chamber walls 404 and/or the coating 400 after deposition, techniques may also be used to maximize the surface-to-volume ratio during of the coating 400 application, including nanotube deposition and nanoparticle deposition. In addition to the above mentioned techniques, the coating material may be deposited in such a way as to create a highly porous material coating.

Figure 5A:
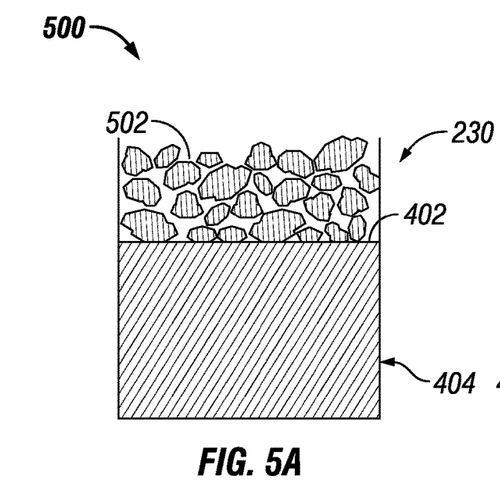
FIG. 5A illustrates an enlarged cross-sectional view of a sample chamber showing an example embodiment of a porous coating.

FIG. 5A illustrates an enlarged cross-sectional view of a sample chamber 230 showing an example embodiment of a porous coating 500. The porous coating 500 may provide, for example, an increased surface-to-volume ratio as compared to non-porous coatings. As illustrated, the porous coating 500 may be deposed on the inner surfaces 402 of the chamber walls 404. While the porous coating 500 is shown with a random distribution of pores 502, it should be understood that the structure and arrangement of the pores 502 should depend on the particular application technique. For example, a porous coating 500 be provided with the pores 502 in a regular distribution (not shown).

Figure 5B:
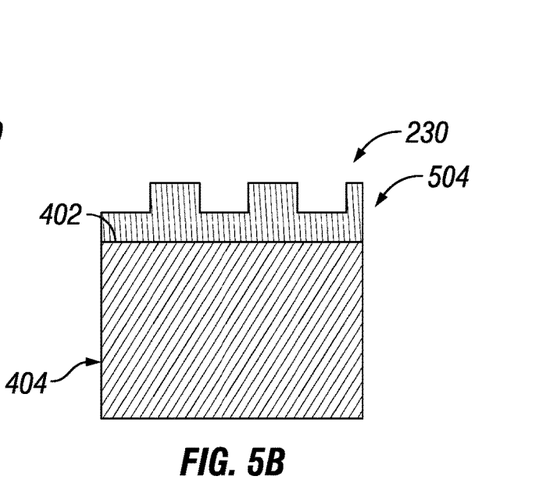
FIG. 5B illustrates an enlarged cross-sectional view of a sample chamber showing an example embodiment of a structured coating.

FIG. 5B illustrates an enlarged cross-sectional view of a sample chamber 230 showing an example embodiment of a structured coating 504. The structured coating 504 may provide, for example, an increased surface-to-volume ratio as compared to non-patterned coating. As illustrated, the structured coating 504 may be deposed on the inner surfaces 402 of the chamber walls 404.

In some embodiments, a protective coating (not shown) may be applied to sample chamber 230 and/or to other components of the fluid sampling tool 170. For example, the protective coating may be applied on the chamber walls 404 underneath the coating 400 such that the coating 400 may be backed by the protective coating. In addition, the protective coating may be applied to other components of the fluid sampling tool 170, such as o-rings, seals, inlet lines (e.g., channel 206 on FIG. 2), inlet valves (e.g., chamber valves 320, 325, 330 on FIG. 3). The protective coating may include any suitable material that is resistant to target component, for example, does not readily adsorb, absorb, or otherwise react to the target component. Suitable materials may include, but are not limited to, aluminum oxide and beryllium oxide, which are both resistant to H2S. One or ordinary skill in the art, with the benefit of this disclosure, should recognize that the specific material for the protective coating should depend on a number of factors, including the particular target component.

Figure 6:
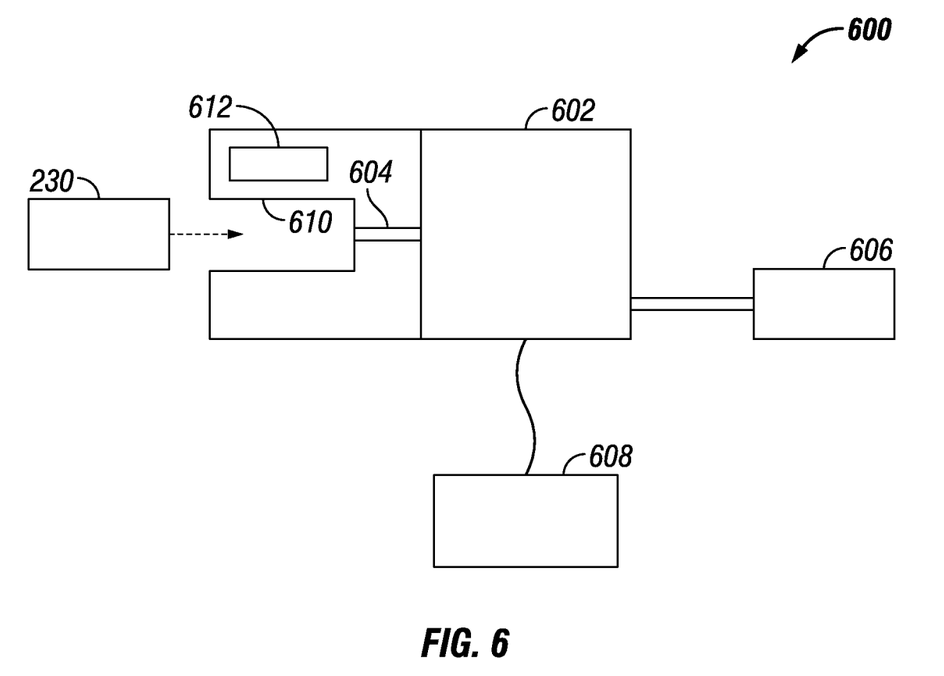
FIG. 6 illustrates an example diagram of an example test system for target component measurement.

FIG. 6 illustrates an example of a test system 600 for target component measurement. As illustrated, the test system 600 may include a chamber housing 602, a fluid analyzer 604, a vacuum pump 606, and a processor 608. Chamber housing 602 may include a chamber receptacle 610 for receiving the sample chamber 230. Sample chamber 230 may contain, for example, a fluid sample of a formation fluid. In some embodiments, the fluid sample may be evacuated from the sample chamber 230 prior to use of test system 600. As previously described, the fluid sample may contain a target component. It may be desired to quantity the concentration of the target component in the fluid sample. In some embodiments, test system 600 may be used for measurement and quantification of the target component in the fluid sample.

In some embodiments, the chamber housing 602 may receive the sample chamber 230 in the chamber receptacle 610. As previously described, the target component may have been sorbed by the coating (e.g., coating 400 on FIG. 4) lining the sample chamber 230. The chamber housing 602 may be operable to desorb the target component from the coating. By way of example, the chamber housing 602 may include a heating element 612. In some embodiments, the heating element 612 may confirm electrical energy into heat. The heat from the heating element 612 may heat the chamber housing 602 such that the target component may be desorbed from the chamber housing 602. While the heating element 612 is shown, it should be understood that the present techniques are intended to encompass other techniques for desorption of the target component from the chamber housing 602. For example, the target component may be chemically stripped from the chamber housing 602.

Test system 600 may further include a fluid analyzer 604 for analyzing the target component after desorption from the chamber housing 602. In the illustrated embodiment, a channel 614 provides fluid communication between the fluid analyzer 604 and the sample chamber 230. Chamber housing 602 may be opened (or otherwise) accessed so that the resorbed target component in the chamber housing 602 can be provided into the fluid analyzer 604 for analysis. As illustrated, a vacuum pump 606 may be used, for example, to create a suction that drives the fluid sample with the desorbed target component from the chamber housing 602 to the fluid analyzer 604. Fluid analyzer 604 may use any of a variety of suitable analysis techniques for analyzing the fluid sample to quantify concentration of the target component. Suitable analysis techniques may include, but are not limited to, gas chromatography, mass spectrometry, and optical sensors.

Test system 600 may further include processor 608. The processor 608 may include any suitable device for processing instructions, including, but not limited to, a microprocessor, microcontroller, embedded microcontroller, programmable digital signal processor, or other programmable device. The processor 608 may also, or instead, be embodied in an application specific integrated circuit, a programmable gate array, programmable array logic, or any other device or combinations of devices operable to process electric signals. The processor 608 may be communicatively coupled to the fluid analyzer 604. The connection between the fluid analyzer 604 and the processor 608 may be a wired connection or a wireless connection, as desired for a particular application.

In some embodiments, the processor 200 can be configured to receive inputs from the fluid analyzer 604, for example, to determine a concentration of the target component in the fluid sample. The fluid analyzer 604, for example, may measure a total quantity (e.g., volume, moles, etc.) of the target component. Since of a total volume of the fluid sample in the sample chamber is known, the concentration of the target component in the fluid sample can then be readily determined with the total quantify of the target component.

In some embodiments, target component measurements may be extrapolated to reservoir conditions. Extrapolation may be performed, for example, using measurements of the target component from more than one sample chamber 230. The fluid sample may be acquired in each of the more than one sample chamber 230 downhole at during the same pump out or at different times. Any suitable technique may be used for extrapolating the target component measurement to reservoir conditions, including, but not limited to, equations of state and geodynamic modeling, among others.

Accordingly, this disclosure describes methods and systems for capture and measurement of a target component. Without limitation, the systems and methods may further be characterized by one or more of the following statements:

Statement 1. A fluid sampling tool for sampling fluid from a subterranean formation may be provided. The fluid sampling tool may include a sample chamber having a fluid inlet, wherein the sample chamber is lined with a coating of a material that can reversibly hold a target component.

Statement 2. The fluid sampling tool of statement 1, wherein the fluid sampling tool further includes a probe that is extendable to engage the subterranean formation from a wellbore, a pump coupled to the probe for pumping fluid from the subterranean formation, wherein the sample chamber is coupled to the pump for receiving a fluid sample pumped from the subterranean formation through the probe.

Statement 3. The fluid sampling tool of statement 1 or 2, further including more than one of the sample chamber.

Statement 4. The fluid sampling tool of any preceding statement, wherein the sample chamber includes a sample fluid including the target component.

Statement 5. The fluid sampling tool of any preceding statement, wherein the target component includes at least one component selected from the group consisting of hydrogen sulfide, mercury, carbon dioxide, and combinations thereof, and wherein the material includes at least one material selected from the group consisting of gold, aluminum oxide, nickel, platinum, and combinations thereof.

Statement 6. The fluid sampling tool of any preceding statement, wherein the coating and/or one or more walls of the sample chamber were treated to increase a surface-to-volume ratio of the coating.

Statement 7. The fluid sampling tool of statement 6, wherein coating and/or the one or more walls were treated with a treatment including at least one lithographic technique selected from the group consisting of etching, anodizing, patterning, and combinations thereof.

Statement 8. The fluid sampling tool of any preceding statement, wherein at least one surface of the fluid sampling tool is coated with a protective coating that is resistant to the target component.

Statement 9. The fluid sampling tool of any preceding statement, wherein the coating is a porous or structured coating.

Statement 10. The fluid sampling tool of any preceding statement, wherein the coating includes gold, wherein the target component includes hydrogen sulfide, and wherein at least one surface of the fluid sampling tool is coated with a protective coating of aluminum oxide that is resistant to the target component.

Statement 11. The fluid sampling tool of any preceding statement, wherein the material is backed with an inert material to the target component.

Statement 12. The fluid sampling tool of statement 11, wherein the inert material includes aluminum oxide, beryllium oxide, or a combination thereof.

Statement 13. A method for sampling formation fluids may be provided. The method may include inserting a sample chamber into a wellbore, wherein the sample chamber is lined with a material that can reversibly hold a target component. The method may further include collecting a fluid sample in the sample chamber while disposed in the wellbore such that the target component in the fluid sample is at least partially sorbed by the material.

Statement 14. The method of statement 13, wherein at least 99% by volume of the target component in the fluid sample is sorbed by the material.

Statement 15. The method of statement 13 or 14, further including retrieving the sample chamber from the wellbore, desorbing the target component from the material, and measuring a quantity of the desorbed target component.

Statement 16. The method of statement 15, wherein the desorbing includes heating the sample chamber.

Statement 17. The method statement 15 may further include collecting one or more additional fluid samples in one or more additional sample chambers while disposed in the wellbore, wherein the one or more additional sample chambers are lined with the material such that at least a portion of the target component present in the one or more additional fluid samples is at least partially sorbed by the material in the one or more additional sample chambers. The method may further include retrieving the one or more additional sample chambers from the wellbore. The method may further include desorbing the target component from the material in the one or more additional samples chambers. The method may further include measuring a quantity of the desorbed component from the one or more additional sample chambers. The method may further include extrapolating the quantity of the desorbed component from the one or more additional sample chambers and the desorbed component from the sample chamber to a reservoir concentration.

Statement 18. The method of any one of statements 13 to 17, wherein the target component includes hydrogen sulfide and the material includes gold, and wherein at least one surface of a fluid sampling tool including the sample chamber is partially coated with a protective coating that is resistant to the target component.

Statement 19. A test system for component measurement may be provided. The test system may include a chamber housing including a chamber receptacle for receiving a sample chamber. The test system may further include a heating element disposed in the chamber housing arranged to heat the sample chamber. The test system may further include a fluid analyzer for measuring a desorbed component from the sample chamber. The test system may further include a vacuum pump in fluid communication with the chamber housing for creating a suction to transfer the desorbed component from the sample chamber to the fluid analyzer. The test system may further include a processor operable to receive inputs from the fluid analyzer to determine a concentration of the desorbed component.

Statement 20. The system of statement 19, wherein the fluid analyzer is selected from a mass spectrometer, a gas chromatograph, an optical sensor, and combinations thereof.

The preceding description provides various embodiments of the systems and methods of use disclosed herein which may contain different method steps and alternative combinations of components. It should be understood that, although individual embodiments may be discussed herein, the present disclosure covers all combinations of the disclosed embodiments, including, without limitation, the different component combinations, method step combinations, and properties of the system. It should be understood that the compositions and methods are described in terms of "including," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present embodiments are well adapted to attain the ends and advantages mentioned as well as those that are inherent therein. The particular embodiments disclosed above are illustrative only, and may be modified and practiced in different but equivalent manners apparent to those skilled in the art having the benefit of the teachings herein. Although individual embodiments are discussed, the disclosure covers all combinations of all of the embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of those embodiments. If there is any conflict in the usages of a word or term in this specification and one or more patent(s) or other documents that may be incorporated herein by reference, the definitions that are consistent with this specification should be adopted.

What is claimed is:

1. A fluid sampling tool for sampling fluid from a subterranean formation, comprising:
   a sample chamber having a fluid inlet, wherein the sample chamber comprises walls lined entirely with a coating of a sorbent material, wherein the sorbent material is a structured or a porous material that increases a surface to volume ratio and consists of gold, nickel, platinum, or combinations thereof;
   a channel fluidically coupled to the sample chamber and a pump;
   a probe, wherein the probe is extendable to engage the subterranean formation from a wellbore; and
   a chamber valve disposed within the channel.

2. The fluid sampling tool of claim 1, wherein the fluid sampling tool further comprises the pump coupled to the probe for pumping fluid from the subterranean formation, wherein the sample chamber is coupled to the pump for receiving a fluid sample pumped from the subterranean formation through the probe.

3. The fluid sampling tool of claim 1, further comprising more than one sample chamber.

4. The fluid sampling tool of claim 1, wherein the sample chamber comprises a sample fluid.

5. The fluid sampling tool of claim 1, wherein a sample fluid comprises at least one component selected from the group consisting of hydrogen sulfide, mercury, carbon dioxide, and combinations thereof.

6. The fluid sampling tool of claim 1, wherein the porous or structured pattern material is formed from at least one lithographic technique selected from the group consisting of etching, anodizing, patterning, and combinations thereof.

7. The fluid sampling tool of claim 1, wherein at least one surface of the fluid sampling tool is coated with a protective coating of aluminum oxide that is resistant to hydrogen sulfide.

8. The fluid sampling tool of claim 1, wherein the sorbent material is backed with an inert material.

9. The fluid sampling tool of claim 8, wherein the inert material comprises aluminum oxide, beryllium oxide, or a combination thereof.

10. The fluid sampling tool of claim 1, further comprising a second valve disposed within the channel, wherein the chamber valve allows a fluid sample to enter the sample chamber and the second valve prevents the fluid sample from directly entering the wellbore.

11. The fluid sampling tool of claim 1, further comprising more than one probe.

12. A method for sampling formation fluids, comprising:
    inserting a sample chamber into a wellbore, wherein the sample chamber comprises walls lined entirely with a coating of a sorbent material, wherein the sorbent material is a structured or a porous material that increases a surface to volume ratio and consist of gold, nickel, platinum, or combinations thereof;
    engaging a probe with the borehole wall, wherein the probe extends from the sample chamber;
    collecting a fluid sample with the probe; and
    placing the fluid sample into the sample chamber while disposed in the wellbore in which the fluid sample is at least partially sorbed by the sorbent material.

13. The method of claim 12, wherein at least 99% by volume of at least one component from the fluid sample selected from the group consisting of hydrogen sulfide, mercury, carbon dioxide, and combinations thereof is sorbed by the sorbent material.

14. The method of claim 12, further comprising retrieving the sample chamber from the wellbore, desorbing the fluid sample from the sorbent material, and measuring a quantity of the desorbed formation fluid.

15. The method of claim 14, wherein the desorbing comprises heating the sample chamber.

16. The method of claim 14, further comprising:
    collecting one or more additional fluid samples in one or more additional sample chambers while disposed in the wellbore, wherein the one or more additional sample chambers are lined with the sorbent material such that at least a portion of the sample fluid present in the one or more additional fluid samples is at least partially sorbed by the sorbent material in the one or more additional sample chambers;
    retrieving the one or more additional sample chambers from the wellbore;

desorbing the sample fluid from the sorbent material in the one or more additional samples chambers;

measuring a quantity of the desorbed component from the one or more additional sample chambers; and extrapolating the quantity of the desorbed component from the one or more additional sample chambers and the desorbed component from the sample chamber to a reservoir concentration.

17. The method of claim 12, wherein the sample fluid comprises hydrogen sulfide and wherein at least one surface of a fluid sampling tool comprising the sample chamber is partially coated with a protective coating that is resistant to the sample fluid.

18. The method of claim 12, further comprising:

heating the sample chamber with a heating element;

measuring a desorbed component with a fluid analyzer from the sample chamber;

creating a suction with a vacuum pump to transfer the desorbed component from the sample chamber to the fluid analyzer; and processing received inputs from the fluid analyzer to determine a concentration of the desorbed component.

19. The method of claim 18, wherein the fluid analyzer is selected from a mass spectrometer, a gas chromatograph, an optical sensor, and combinations thereof.

20. The method of claim 12, wherein the sorbent material is backed with an inert material that comprises aluminum oxide, beryllium oxide, or a combination thereof.

* * * * *